(12) United States Patent
Collard et al.

(10) Patent No.: US 12,292,372 B2
(45) Date of Patent: May 6, 2025

(54) MEASURING DEVICE AND METHOD FOR MEASURING CHARACTERISTICS OF CELLS

(71) Applicants: CENTRE NATIONAL DE LA RECHERCHE SCIENTIFIQUE (CNRS), Paris (FR); JUNIA, Lille (FR)

(72) Inventors: Dominique Collard, Lambersart (FR); Hiroyuki Fujita, Tokyo (JP); Stanislav Karsten, Rancho Palos Verdes, CA (US); Mehmet Cagatay Tarhan, Lambersart (FR)

(73) Assignees: CENTRE NATIONAL DE LA RECHERCHE SCIENTIFIQUE (CNRS), Paris (FR); JUNIA, Lille (FR)

( * ) Notice: Subject to any disclaimer, the term of this patent is extended or adjusted under 35 U.S.C. 154(b) by 27 days.

(21) Appl. No.: 17/766,562

(22) PCT Filed: Oct. 6, 2020

(86) PCT No.: PCT/EP2020/078007
§ 371 (c)(1),
(2) Date: Apr. 5, 2022

(87) PCT Pub. No.: WO2021/069446
PCT Pub. Date: Apr. 15, 2021

(65) Prior Publication Data
US 2024/0102915 A1    Mar. 28, 2024

(30) Foreign Application Priority Data

Oct. 8, 2019 (EP) ..................................... 19306313

(51) Int. Cl.
*G01N 15/14* (2024.01)
*B01L 3/00* (2006.01)
(Continued)

(52) U.S. Cl.
CPC .... *G01N 15/1484* (2013.01); *B01L 3/502761* (2013.01); *G01N 15/1031* (2013.01);
(Continued)

(58) Field of Classification Search
None
See application file for complete search history.

(56) References Cited

U.S. PATENT DOCUMENTS

| 7,086,502 B2 * | 8/2006 | Yim ....................... A63B 27/00 |
| | | 182/136 |
| 8,978,792 B2 * | 3/2015 | Fauroux ............... B62D 57/024 |
| | | 180/8.1 |

(Continued)

FOREIGN PATENT DOCUMENTS

| CN | 108731720 A | * | 11/2018 | ........... G01D 11/245 |
| CN | 208907814 U | * | 5/2019 | ........... G01D 11/245 |
| CN | 110108843 A | * | 8/2019 | |

*Primary Examiner* — Jamel E Williams
(74) *Attorney, Agent, or Firm* — Arrigo, Lee, Guttman & Mouta-Bellum LLP

(57) ABSTRACT

The invention relates to a measuring device (10) for measuring physical characteristics of cells. The device (10) comprises: a microfluidic chip (20) provided with a flow channel (22) for allowing cells to flow through; a manipulator (24) configured to apply deformation force to a cell in a continuous flow; and a sensor (26) configured to sense a physical characteristic of the cell. The manipulator (24) and the sensor (26) are configured to define a width (W2) of the flow channel (22) as a gap formed between them. The manipulator (24) is configured to apply the deformation force to the cell by compressing the cell against the sensor (26).

16 Claims, 5 Drawing Sheets

(51) Int. Cl.
*G01N 15/1031* (2024.01)
*G01N 33/487* (2006.01)
*G01N 15/10* (2006.01)

(52) U.S. Cl.
CPC .............................. *G01N 33/48728* (2013.01); *B01L 2200/0663* (2013.01); *B01L 2300/0645* (2013.01); *G01N 2015/1006* (2013.01); *G01N 2015/1495* (2013.01)

(56) References Cited

U.S. PATENT DOCUMENTS

| | | | |
|---|---|---|---|
| 2009/0280518 A1* | 11/2009 | Adamo | G01N 33/48728 324/92 |
| 2014/0128285 A1* | 5/2014 | Rowat | G01N 29/222 506/10 |
| 2017/0180612 A1* | 6/2017 | Marashdeh | H04N 7/181 |
| 2017/0227453 A1* | 8/2017 | Scipolo | G01N 33/005 |
| 2017/0336061 A1* | 11/2017 | Riedel | B64F 1/00 |

* cited by examiner

MEASURING DEVICE AND METHOD FOR MEASURING CHARACTERISTICS OF CELLS

FIELD OF THE INVENTION

The present invention relates to a measuring device used for biophysical characterization of cells and to a method for measuring biophysical characterization of cells. Physical characterization of cells is relevant to the field of cytology, in particular for biological and/or medical studies.

BACKGROUND OF THE INVENTION

In the field of biomedical sciences, there has been a great demand for solutions to determine biophysical characteristics of individual cells. The biophysical characteristics of cells provide useful information to identify a relationship between the cell and a certain disease, such as cancer.

For this purpose, measuring devices have been proposed to identify physical properties of individual cells in a continuous manner. For example, WO 2018/108880 discloses an integrated system comprising a microfluidic chip formed with a microfluidic channel and sensor means for directly manipulating a single cell to obtain its biophysical characteristics by introducing the sensor means into the channel through a lateral opening. This technique is advantageous as it is cost-effective, compared to other known techniques involving expensive antibody-specific labelling, for example, and also able to maintain the cells unaltered for a further analysis.

There is also disclosed an integrated microfluidic chip for measuring cell mechanical characteristics by KOU NAKAMURA ET AL in "On-Chip Transportation and Measurement of Mechanical Characteristics of Oocytes in an Open Environment", MICROMACHINES, vol. 6, no. 5, May 22, 2015, pages 648-659, XP055679175, DOI: 10.3390/mi6050648.

However, according to the teachings of WO 2018/108880 and "KOU NAKAMURA ET AL", each cell has to be captured and manipulated by tweezers, which requires a significant time, e.g. one minute or even more per a single cell, until a high content analysis, i.e. a comprehensive and reliable electromechanical analysis, is done.

US 2009/280518 A1, US 2019/227021 A1 and WO 2018/207087 disclose systems adapted for measuring physical characteristics of cells without requiring the individual cells to be captured. However, these known systems are not adapted to obtain physical characteristics of the cells in a continuous manner while the cells are being subjected to deformation force.

In view of the above limitation of the existing system, the objective of the present invention is to provide a measuring device and a measuring method which can improve performance with increased throughput for a high content analysis.

SUMMARY OF THE INVENTION

According to the invention, there are provided a measuring system and a measuring method as defined in appended independent claims and the corresponding dependent claims.

Specifically, there is disclosed a measuring device for measuring physical characteristics of cells, the measuring device comprising: a microfluidic chip provided with a flow channel for allowing cells to flow through from one end to another end of the flow channel, the flow channel including an inlet part, a characterization part and an outlet part; a manipulator situated in the characterization part between the inlet part and the outlet part of the flow channel and configured to manipulate a cell in a continuous flow through the characterization part by applying deformation force to the cell in the characterization part; and a sensor situated in the characterization part and configured to sense a physical characteristic of the cell in the characterization part of the flow channel, wherein the manipulator and the sensor are configured to define a width of the characterization part of the flow channel as a gap formed between the manipulator and the sensor, the width being smaller than the size of the cell, and wherein the manipulator is configured to apply the deformation force to the cell by compressing the cell against the sensor.

There is also disclosed the measuring device, wherein the manipulator comprises a movable unit configured to move within the flow channel relative to the sensor so that the width of the characterization part of the flow channel is variable.

There is also disclosed the measuring device, wherein the manipulator extends over a distance ranging from 10 μm to 1000 μm along the flow channel.

There is also disclosed the measuring device, wherein the manipulator comprises a guiding portion and a tip portion, the guiding portion being inclined toward the sensor to define a decreasing gap between the manipulator and the sensor, the tip portion extending parallel to the sensor to define a constant gap between the manipulator and the sensor.

There is also disclosed the measuring device, wherein the manipulator comprises a protrusion protruding within the flow channel, the protrusion protruding toward the sensor such that the width of the characterization part of the flow channel is formed as a gap formed between the protrusion and the sensor.

There is also disclosed the measuring device, wherein the protrusion is configured such that the width of the characterization part of the flow channel gradually decreases along the flow channel.

There is also disclosed the measuring device, wherein the manipulator extends over a distance ranging from 10 μm to 500 μm along the flow channel.

There is also disclosed the measuring device further comprising a further sensor situated in the inlet part which is upstream of the characterization part and configured to detect the size of a cell in the inlet part of the flow channel.

There is also disclosed the measuring device, wherein the manipulator is configured to control a position of the movable unit within the flow channel to adjust the width of the characterization part of the flow channel, depending on the size of the cell detected by the further sensor.

There is also disclosed the measuring device further comprising a further sensor configured to detect the size of a cell within the flow channel.

There is also disclosed the measuring device, wherein the further sensor is configured to optically, magnetically or electrically detect the size of the cell.

There is also disclosed the measuring device, wherein the sensor is further configured to sense mechanical and/or electrical characteristics of the cell in the characterization part of the flow channel.

There is also disclosed the measuring device, wherein the sensor includes a plurality of electrodes.

There is also disclosed the measuring device further comprising at least one additional sensor and at least one additional manipulator, both of which are situated in an additional characterization part downstream of the characterization part of the flow channel.

There is also disclosed the measuring device, wherein the at least one additional manipulator is configured to apply deformation force to the cell in the additional characterization part of the flow channel, the deformation force applied by the additional manipulator being different in magnitude from the deformation force applied by the manipulator.

There is also disclosed a method for measuring physical characteristics of cells, comprising: providing cells to a flow channel which is designed to allow the cells to continuously flow within the flow channel, detecting the size of a cell flowing within the flow channel; compressing the cell in a continuous flow in the follow channel by a portion of the flow channel whose width is defined by a gap between a manipulator and a sensor, the width being smaller than the size of the cell; and sensing mechanical and/or electrical characteristics of the cell by the sensor, while compressing the cell between the manipulator and the sensor.

There is also disclosed the method, wherein the compressing includes controlling deformation force applied by the manipulator to the cell, depending on the size of the cell detected prior to the compressing.

Furthermore, the present application discloses a measuring device for measuring physical characteristics of cells, the measuring device comprising: a microfluidic chip provided with a flow channel for allowing cells to flow through from one end to another end of the flow channel, the flow channel including an inlet part, a characterization part and an outlet part; application means situated in the characterization part between the inlet part and the outlet part of the flow channel and configured to apply deformation force to a cell in the characterization part of the flow channel; and sensing means situated in the characterization part and configured to sense a physical characteristic of the cell in the characterization part of the flow channel, wherein the application means and the sensing means are configured to define a width of the characterization part of the flow channel, and wherein the characterization part is configured to allow a cell to flow while applying the deformation force to the cell.

The application means may comprise a movable unit configured to move within the flow channel relative to the sensing means so that the width of the characterization part of the flow channel is variable.

The application means may extend over a distance ranging from 10 μm to 1000 μm along the flow channel.

The application means may comprise a protrusion protruding within the flow channel.

The protrusion may be configured such that the width of the characterization part of the flow channel gradually decreases along the flow channel.

The application means may extend over a distance ranging from 10 μm to 500 μm along the flow channel.

The measuring device may further comprise a size detection means situated in the inlet part which is upstream of the characterization part and configured to detect the size of a cell in the inlet part of the flow channel, wherein the application means is configured to control a position of the movable unit within the flow channel to adjust the width of the characterization part of the flow channel, depending on the size of the cell detected by the size detection means.

The measuring device may further comprise a size detection means configured to detect the size of a cell within the flow channel.

The size detection means may be configured to optically or electrically detect the size of the cell.

The sensing means may be further configured to sense mechanical and/or electrical characteristics of the cell in the characterization part of the flow channel.

The sensing means may include a plurality of electrodes.

The measuring device may further comprise at least one additional sensing means and at least one application means, both of which are situated in an additional characterization part downstream of the characterization part of the flow channel.

The at least one additional application means may be configured to apply deformation force to a cell in the additional characterization part of the flow channel, the deformation force applied by the additional application means being different in magnitude from the deformation force applied by the application means.

The present application also discloses a method for measuring physical characteristics of cells, comprising the steps of: providing cells to a flow channel which is designed to allow the cells to continuously flow within the flow channel, detecting the size of a cell flowing within the flow channel; compressing the cell by a portion of the flow channel whose width is smaller than the size of the cell; and sensing mechanical and/or electrical characteristics of the cell under influence of the compression.

The compressing step may include controlling deformation force applied to the cell, depending on the size of the cell detected in the detecting step.

BRIEF DESCRIPTION OF THE FIGURES

Embodiments of the invention will be described in further detail with reference to the accompanying drawings, in which.

DETAILED DESCRIPTION OF EMBODIMENTS OF THE INVENTION

Measuring devices explained hereinafter are designed to measure physical characteristics of individual cells. The respective measuring devices may be configured as a cell cytometer. A cell population from which cells are taken as measurement objects may be complex heterogeneous cells mixtures and tissues, which include but are not limited to any complex multicellular mixture, such as complex cell cultures, cell spreads, tissue sections (e.g. brain tissues), liquid biopsies, dissociated cells from solid biopsies. Any known sorting means (e.g. laser or labelling) and collecting means (e.g. vacuum or pipetting) can be used to acquire individual cells from cell populations before introducing them to the measuring device.

Figure 1:
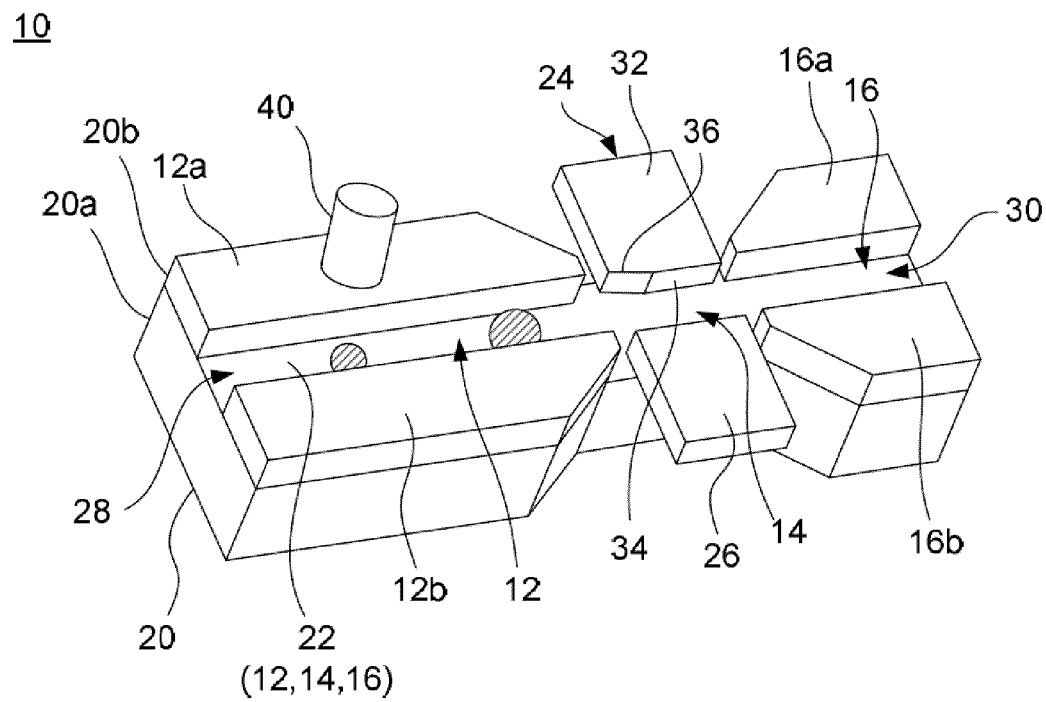
FIG. 1 is a perspective view showing a measuring device.
Figure 2:
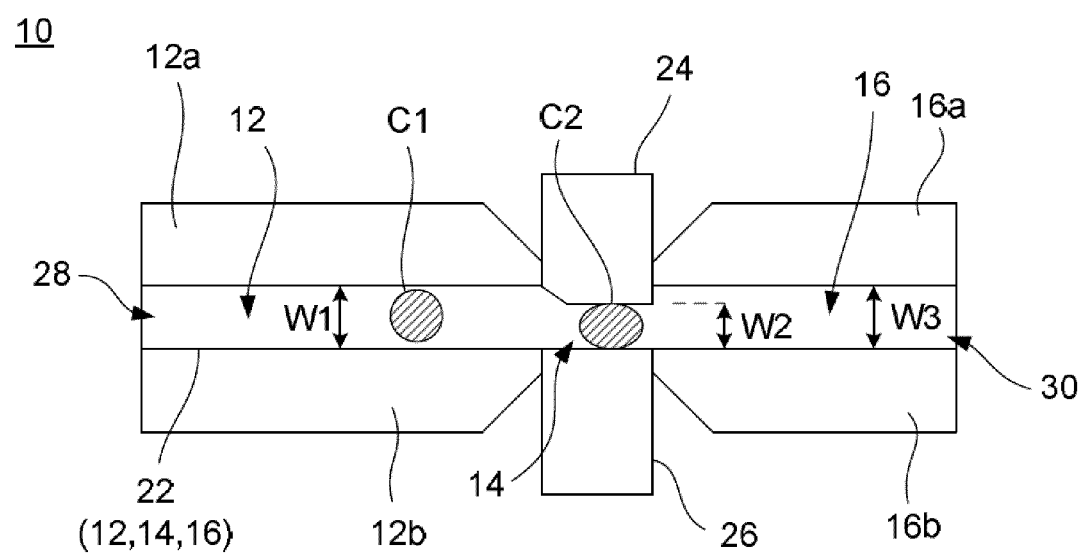
FIG. 2 is a plan view of the measuring device of FIG. 1, showing a cell being compressed within a flow channel.

Referring to FIGS. 1 and 2, the configuration of a measuring device 10 is shown by way of example. The measuring device 10 comprises a microfluidic chip 20 provided with a flow channel 22, an application means 24 and a sensing means 26. The microfluidic chip 20 is generally in the form of a flat plate having a layered structure. The microfluidic chip 20 includes a base layer 20a made of glass or silicon, and a patterned main body layer 20b made of oxide or silicon and formed on top of the base layer 20a. The base layer 20a and the main body layer 20b may be both formed by silicon micromachining technique.

The base layer 20a and the main body layer 20b may also be made of known conductive polymers or metals. The base layer 20a and the main body layer 20b may be formed by 3D printing techniques. However, other manufacturing techniques may also be used, such as laser micromachining, which is suitable to various metals.

Although not illustrated in the drawings, the base layer 20a may comprise an oxide layer on which the main body layer 20b is formed. The oxide layer may be etched away in a portion below movable components of the measuring device 10, e.g. the sensing means 26 and a movable unit 32, which is further explained below. With this configuration, the oxide layer serves as a spacer allowing those movable components to move freely. Such an oxide layer may also provide electrical insulation from the main body layer 20b.

The flow channel 22 is a generally longitudinal microfluidic channel. The flow channel 22 is not limited to any particular shape and may be a straight channel, a curved channel or a bent channel, or any combination thereof.

The flow channel 22 includes an inlet part 12, a characterization part 14, and an outlet part 16, which are in fluid communication with each other. As further explained below, the application means 24, which may also be referred to as "manipulator", and the sensing means 26, which may also be referred to as "sensor", together form the characterization part 14 of the flow channel 22.

The inlet part 12 of the flow channel 22 is provided upstream of a cell flow relative to the characterization part 14 and the outlet part 16. Cells to be characterized by the measuring device 10 are introduced from a first end 28 in the inlet part 12. The inlet part 12 is defined by a top surface of the base layer 20a, first body parts 12a and 12b in the main body layer 20b, and a top cover (not illustrated) placed over the first body parts 12a and 12b. A spacer (not illustrated) is provided between the first body parts 12a and 12b and the top cover. The spacer is configured to allow the movable components to move freely relative to the static parts of the measuring device 10, while providing required sealing. The top cover may be made of polydimethylsiloxane (PDMS). Other suitable materials may also be used to make the top cover, including but not limited to glass, quartz, polycarbonate, PMMA (polymethyl methacrylate) or silicon. Transparent materials may be used for the top cover in particular if the top cover is required to be optically accessible.

The inlet part 12 of the flow channel 22 is designed to allow individual cells to flow from the first end 28 into the characterization part 14. More specifically, the first body parts 12a and 12b are patterned to together define a width W1 of the inlet part 12 of the flow channel 22 (see FIG. 2). The width W1 of the inlet part 12 is determined so as to be large enough for cells to continuously flow without going through a substantial deformation.

In an embodiment, the width W1 may also be designed to be small enough to prevent more than one cells from flowing together within the inlet part 12. In other words, the flow channel 22 is designed such that a single cell at a time can flow at a particular position of the inlet part 12. In another embodiment, the cell flow is controlled at the inlet part 12 in such a way that only a single cell flows in the flow channel 22, irrespective of the width W1 of the inlet part 12. This may be done by controlling the timing of introducing cells.

The characterization part 14 is situated between the inlet part 12 and the outlet part 16. The configuration of the characterization part 14 will be explained below in more detail.

The outlet part 16 is provided downstream of the cell flow relative to the inlet part 12 and the characterization part 14. A second end 30 of the flow channel 22 is formed in the outlet part 16 where the measuring device 10 may be configured to cooperate with other devices, such as a sorting device, a collecting tool or other testing devices, in order to carry out a further analysis of the cells as necessary.

In the same way as the inlet part 12, the outlet part 16 of the flow channel 22 is defined by the top surface of the base layer 20a, second body parts 16a and 16b in the main body layer 20b and the top cover. The outlet part 16 defines a width W3 of the flow channel 22 between the second body parts 16a and 16b (see FIG. 2). In an embodiment, the width W3 of the outlet part 16 may be substantially the same as the width W1 of the inlet part 12. In another embodiment, the width W3 may be determined, depending on the requirement of a further process, including but not limited to sorting, collecting or a biological analysis. For example, the width W3 may be determined, depending on the size of a sorting or collecting device or an analytical tool, which are provided in or introduced into the downstream part of the outlet part 16.

At the characterization part 14, the application means 24 is provided on one side of the flow channel 22 and the sensing means 26 is provided on the other side of the flow channel 22.

The application means 24 further comprises a movable unit 32 and a controller (not illustrated) for controlling movement of the movable unit 32. In an embodiment the movable unit 32 may be an actuatable electrode. The movable unit 32 generally has a flat tip portion 34 which forms an innermost portion of the application means 24. The movable unit 32 is formed with a guiding portion 36 extending from the tip portion 34 toward the upstream side, in order to facilitate the cells flowing into a gap between the tip portion 34 of the movable part 32 and the sensing means 26.

The movable unit 32 is configured to move in a direction substantially perpendicular to a cell flow direction, i.e. in a direction toward the sensing means 26 and in the other direction away from the sensing means 26. With this configuration, a width W2 of the characterization part 14 of the flow channel 22, i.e. the gap between the application means 24 and the sensing means 26, depends on the position of the movable unit 32. Therefore, the width W2 is variable and adjustable in response to a control signal from the controller.

The guiding portion 36 may be inclined toward the sensing means 26, thereby defining a decreasing gap between the application means 24 and sensing means 26. The tip portion 34 may extend parallel to the sensing means 24, thereby defining a constant gap between the application means 24 and the sensing means 26.

In other embodiments, a further guiding portion may be formed on an opposite side of the tip portion 34 from the guiding portion 36, or the downstream of the tip portion 34. The further guiding portion (not shown) may be inclined away from the sensing means 26, thereby defining an increasing gap between the application means 24 and the sensing means 26.

In an embodiment, for the purpose of physical characterization of the cells, the width W2 is chosen to be a given value which is smaller than the diameter of the cell, in order to ensure that a cell flowing through the characterization part 14 is compressed by the application means 24 and subjected to a controllable degree of deformation. The deformation level may be set to any given level, including but not limited to 5%, 10%, 15%, 20%, 25% or 30% of the original cell size.

The application means 24 is configured to manipulate a cell in a continuous flow through the characterization part 14, i.e. without interrupting the cell flow in the characterization part 14, by applying deformation force to the cell. The deformation force is applied by compressing the cell against the sensing means 26.

The application means 24 and the sensing means 26 are dimensioned with respect to the direction parallel to the flow channel 22, in particular in relation to the first body parts 12a and 12b as well as the second body parts 16a and 16b such that the movable unit 32 can smoothly move relative to the first and second body parts 12a, 12b, 16a and 16b and at the same time leakage of the cell media from the flow channel 22 can be prevented.

In an embodiment, the dimension of the tip portion 34 of the movable unit 32 along the flow channel 22 may be within a range from 10 μm to 1000 μm.

The sensing means 26 is configured to sense a mechanical characteristic of a cell present in the characterization part 14. The sensing means 26 may be a mechanical sensing electrode configured as a resonance actuator. When a cell is present in the characterization part 14, a shift of the resonance frequency occurs as the cell comes in contact with the sensing means 26. Based on the resonance frequency shift, mechanical characteristics of the cell, such as stiffness, viscosity and viscoelastic response, can be determined. In another embodiment, the sensing means 26 may also be configured as a passive displacement sensor.

Alternatively or in addition to the above configuration, the sensing means 26 may also be configured to sense electrical characteristics of the cell. In this case, the application means 24 is configured to transmit an electric signal, which is detected by the sensing means 26 through electrodes. An electrical impedance of the cell, i.e. the membrane capacitance and cytoplasm conductivity, can be acquired under conditions with various frequencies of electric signals for the cell which undergoes a controllable degree of deformation.

In the embodiment where the mechanical characterization as well as the electrical characterization takes place by the same sensing means 26, it is preferable that the frequency ranges of mechanical actuation and of electrical signals do not overlap with each other. For example, a resonance frequency for mechanical sensing may be set within a range from 1 to 100 kHz, while the frequency of electric signals may be set within a range from 0.1 to 10 MHz. In this way, a cross talk which could otherwise occur during the simultaneous mechanical and electrical characterizations can be avoided.

In an embodiment, the measuring device 10 may also comprise a size detection means 40, which may also be referred to as "further sensor", at a position corresponding to the inlet part 12 of the flow channel 22. The size detection means 40 may be any known type of size detection tool or device. The size detection means 40 is configured to detect the size of a cell within the flow channel 22. Since the width W1 of the inlet part 12 is larger than the cell, the size detection means 40 can detect the size of the cell which is not subjected to a deformation. Further, the size detection means 40 is designed to perform the size determination of flowing cells, or in other words does not affect a continuous cell flow in the inlet part 12 of the flow channel 22.

In an embodiment, the size detection means 40 may be an optical sensor configured to optically detect the size of the cell. For example, the size determination can be carried out by capturing an image of the cell by a camera provided over the inlet part 12 of the flow channel 22 and then processing the corresponding image date in accordance with a known image processing technique.

Figure 3:
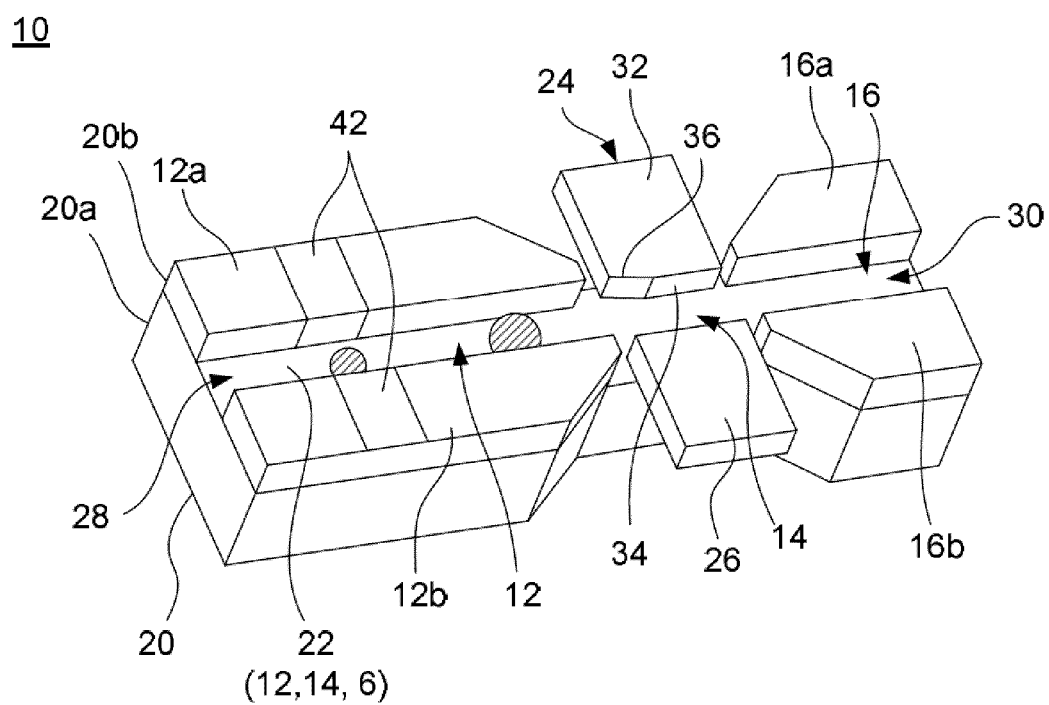
FIG. 3 is a perspective view showing another measuring device.

In other embodiments, the size detection means 40 may be an electrical sensor configured to electrically detect the size of the cell. Referring to FIG. 3, an embodiment is shown where an electrical sensor 42 is provided in the inlet part 12 of the flow channel 22. For example, the size determination can be carried out based on a change in electrical conductivity resulting from the presence of a flowing cell.

In other embodiments, the size detection means 40 may be a magnetic sensor configured to magnetically detect the size of the cell.

The size detection means 40 may be integrally formed with the measuring device 10 or provided independently of the measuring device 10.

In an embodiment where the size detection means 40 is provided at or near the inlet part 12 of the flow channel 22, the controller of the application means 24 may be configured to control the position of the movable unit 32 thereby adjusting the width W2 of the flow channel 22, or the gap between the application means 24 and the sensing means 26, depending on the size of the cell detected by the size detection means 40.

A method for measuring physical characteristics of cells using the measuring device 10 will be explained.

Individual cells to be subjected to the required characterization are separated from each other and obtained from cell mixtures.

Those cells are introduced into the measuring device 10 from the first end 28 of the flow channel 22. In order to produce a continuous cell flow in the flow channel 22, appropriate cell media is also supplied from the first end 28 of the flow channel 22.

After entry into the flow channel 22, a cell passes the inlet part 12 of the flow channel 22 where the size of the cell (refer to "cell C1" in FIG. 2) is determined by the size detection means 40. During the size determination, the cell C1 continuously flows toward the second end 30 without interruption since the width W1 of the inlet part 12 is larger than the cell size.

Optionally, the information on the size of the cell C1 detected in the inlet part 12 may be transmitted to the controller of the application means 24. Then, the application means 24 controls the position of the movable part 32, depending on the information corresponding to the cell size, in order to adjust the width W2 of the characterization part 14 of the flow channel 22, thereby applying a controlled deformation force to the cell (see "cell C2" in FIG. 2).

Since the width W2 of the characterization part 14 is determined such that the cell passing therethrough is subjected to deformation force by the flow channel 22 and deformed to a certain degree and such that the cell can continuously flow toward the second end 30 of the flow channel 22. As the cell moves along the characterization part 14 of the flow channel 22, the sensing means 26 obtains mechanical and/or electrical characteristics of the cell under the influence of deformation force. In this way, the mechanical and/or electrical characteristics of the cell can be obtained while the cell is being compressed between the application means 24 and the sensing means 26.

The width W2 of the characterization part 14 may be determined such that the cell flowing through the characterization part 14 is deformed in a range from 5% to 30% of the original size.

The information on the mechanical and/or electrical characteristic obtained in the characterization part 14 may be stored in a storage device (not illustrated) or transmitted to an external device for a further analysis.

After the physical characterization, the cell continues to flow to the second end 30 of the flow channel 22 where the cell is collected or sorted, depending on the obtained characteristics.

Thanks to the configuration of the measuring device 10 as described above, the physical characteristics of individual cells can be identified as the cells flow through the measuring device 10 without an interruption. Therefore, the physical characterization can be carried out for one cell after another. As a result, the time required for biophysical characterization for individual cells can be advantageously reduced to less than one second, e.g. one to ten milliseconds.

Further, since the width W2 of the characterization part 14 is adjustable and yet can be precisely controlled for each individual cell, the same condition for characterization of the cells can be easily reproduced, thereby facilitating comparison of the result of the physical characterization.

Moreover, according to the disclosed system and method, the physical characteristics of the cell can be continuously obtained even while the cell is being subjected to the deformation force. Therefore, it is possible to conduct a high content analysis of the cells.

Therefore, according to the disclosed technique, significant improvement in throughput of the reliable high content analysis can be achieved.

According to the disclosed system and method, the mechanical manipulation can be done through the direct contact between the cell and the sensing means 26. In this way, the mechanical response of the cell to the manipulation, i.e. the mechanical characteristics of the cell, can be precisely obtained.

Figure 4:
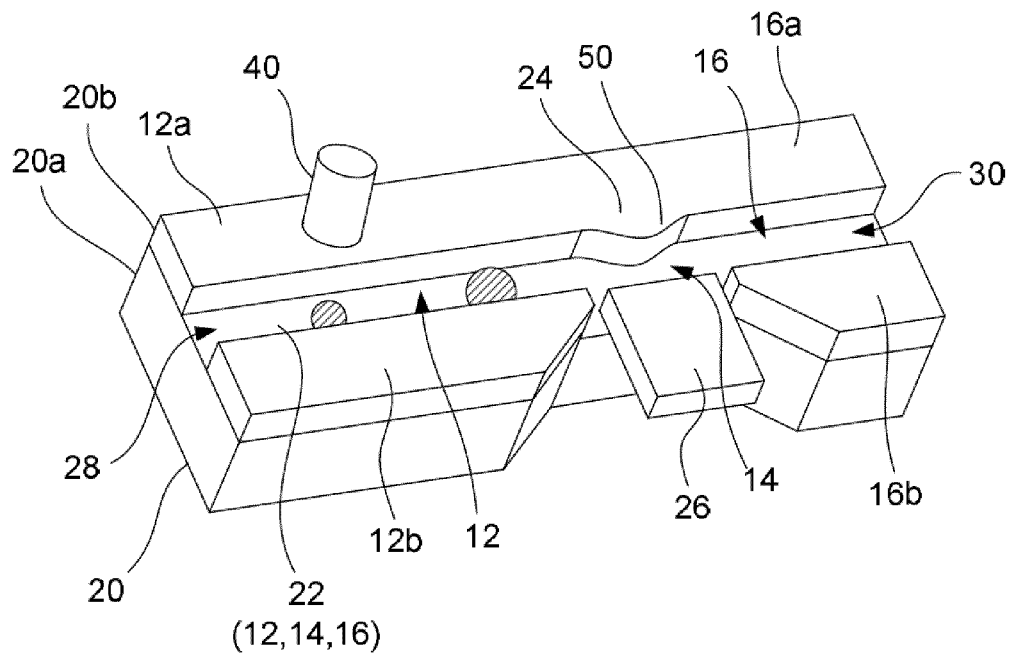
FIG. 4 is a perspective view showing yet another measuring device.
Figure 5:
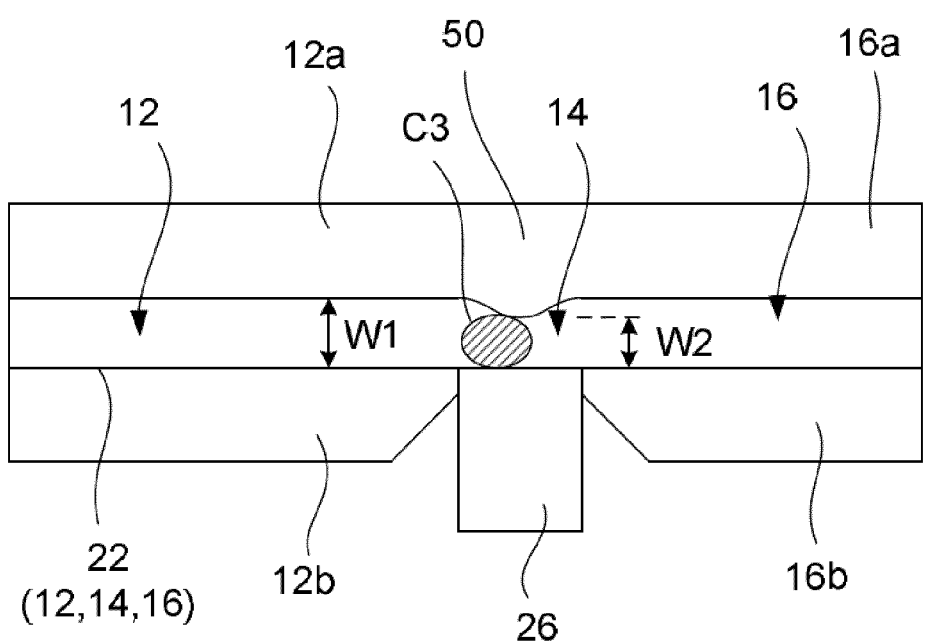
FIG. 5 is a plan view of the measuring device of FIG. 4, showing a cell being compressed within a flow channel.

FIGS. 4 and 5 show another measuring device 10. The measuring device 10 comprises an application means 24 having a different configuration. The application means 24 is in the form of a protrusion 50 protruding from one of the body parts 12a toward the sensing means 26. In other words, the flow channel 22 is formed to become narrower in the characterization part 14 than the inlet part 12 and the outlet part 16.

The protrusion 50 protrude toward the sensor 26 such that the width W2 of the characterization part 14 of the flow channel 22 is formed as a gap formed between the protrusion 50 and the sensor 26.

In an embodiment, the protrusion 50 may have an arc shape having one curvature. In another embodiment, the protrusion 50 may have a curved surface having more than one curvature.

In such a way, the width W2 of the characterization part 14 of the flow channel 22 gradually decreases along the flow channel 22 up to an innermost point of the protrusion 50 and gradually increases again along the flow channel 22. In an embodiment, the protrusion 50 may extend over a distance ranging from 10 μm to 500 μm along the flow channel 22.

Thanks to this configuration of the characterization part 14, when the cell C3 reaches the characterization part 14 of the flow channel 22, the cell C3 is compressed at a predetermined speed according to the profile of the protrusion 50.

Therefore, the mechanical and electrical characterization of the cells at the various levels of deformation can be carried out. In addition to the increased throughput resulting from the continuous cell flow, the great deal of information can be obtained by the measuring device 10.

In addition, in an embodiment where the size detection means 40 is further provided in the inlet part 12, high content information including a combination of the cell size, the mechanical and electrical characterization of the cells can be obtained by the measuring device 10.

Figure 6:
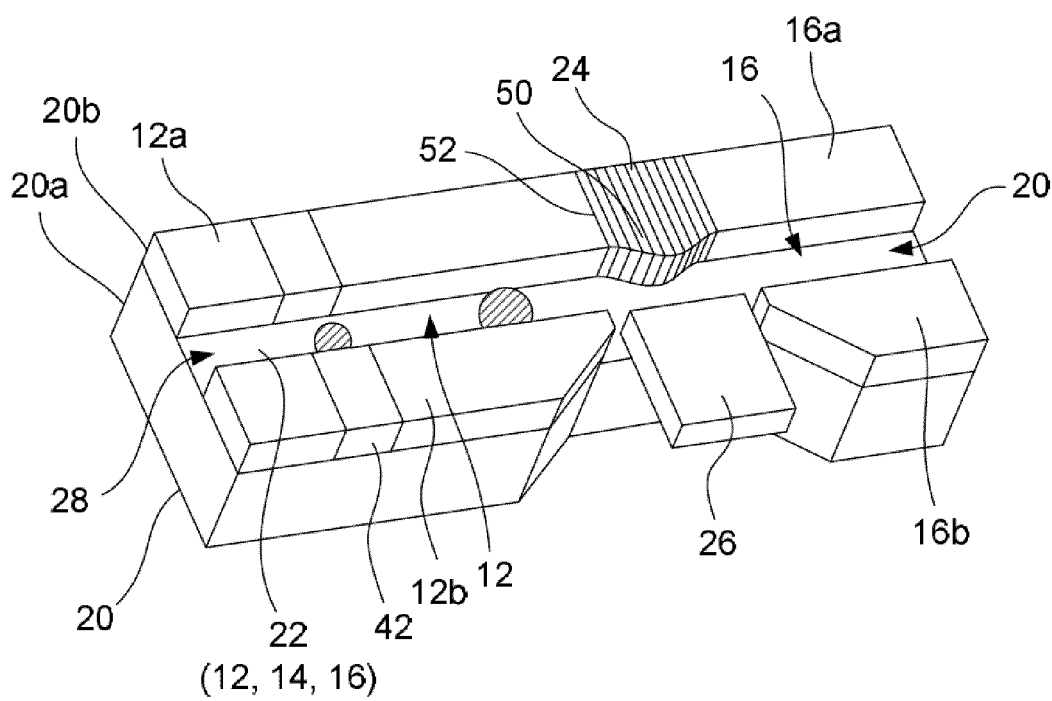
FIG. 6 is a perspective view showing yet another measuring device.

Referring to FIG. 6, the application means 24 according to an embodiment may comprise a plurality of electrodes 52 patterned on the full or a partial length of the characterization part 14. The electrodes 52 are configured to detect the cell impedance continuously as the cell flows in the characterization part 14. According to this configuration, the electrodes 52 can also provide the cell size measurement in place of the size detection means 40 or the electrical sensor 42 described above.

Since the electrodes 52 are arranged in the characterization part 14, the electrical characterization of the cell can be carried out at the various levels of deformation.

Figure 7:
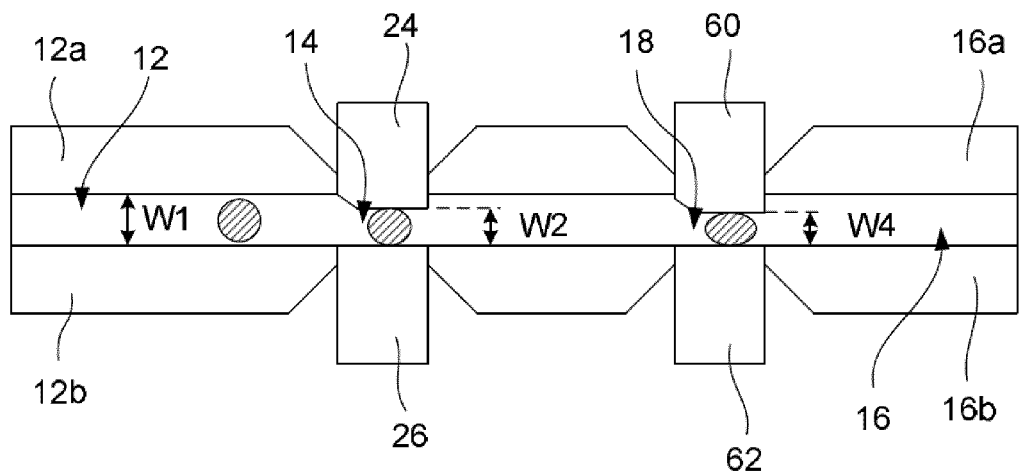
FIG. 7 is a plan view showing yet another measuring device.

FIG. 7 shows another measuring device 10 comprising, in addition to the application means 24 and the sensing means 26 (hereinafter referred to as "the first application means" and "the first sensing means" respectively), an additional application means, or a second application means 60, and an additional sensing means, or a second sensing means 62. The second application means 60 and the second sensing means 62 are situated in the second characterization part 18 of the flow channel 22 which is downstream of the first characterization part 14. The width W4 between the second application means 60 and the second sensing means 62 can be adjusted independently of the first application means 24.

The second application means 60 may be configured to compress the cell at a given level (magnitude) which is different from that of the first application means 24. For example, the first application means 24 may be configured to apply deformation force to the cell in the first characterization part 14 to reduce the size of the cell by 10%, while the second application means 60 may be configured to apply deformation force to the cell in the second characterization part 18 to reduce the size of the cell by 20%.

According to this configuration, characterization of cells at different levels of deformation can be carried out by the single unit.

The number of pairs of the application means and the sensing means is not limited to two, rather any number of the application means and the corresponding sensing means may be provided as necessary.

Figure 8:
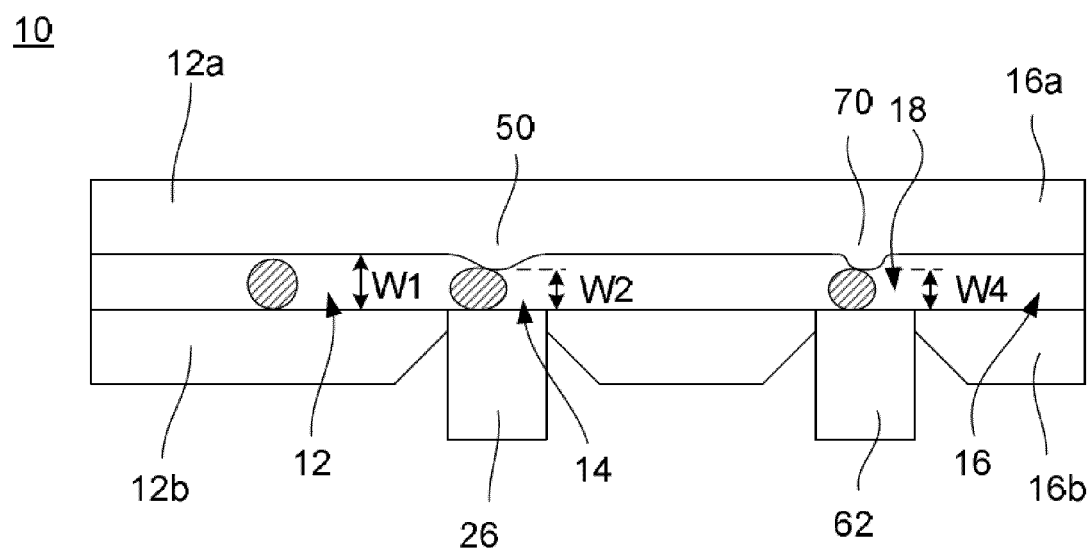
FIG. 8 is a plan view showing yet another measuring device.

FIG. 8 shows another measuring device 10. The measuring device 10 comprises, in addition to the protrusion 50 extending over the first characterization part 14 of the flow channel 22, another protrusion 70 formed in a second characterization part 18 and the corresponding second sensing means 62.

The protrusion 70 in the second characterization part 18 has a profile different from that of the first characterization part 14, in such a way that the cells flowing through the first and second characterization parts 14 and 18 are compressed at different speeds.

According to this configuration, characterization of cells at different compression speeds can be carried out by the single unit.

The number of pairs of the application means and the sensing means is not limited to two, rather any number of the application means and the corresponding sensing means may be provided as necessary.

In an embodiment, the measuring device may comprise two or more pairs of application means and sensing means, of which at least one application means includes a movable unit as described above referring to FIGS. 1 to 3 and at least one application means includes a protrusion as described above referring to FIGS. 4 to 6.

In an embodiment, the flow channel 22 may comprise at least one sub-channel (not illustrated). The sub-channel may be provided in the inlet part 12 and/or in the outlet part 16. In the embodiment where two or more pairs of the application means and sensing means are provided (i.e. there are two or more characterization parts), the sub-channel may be provided between adjacent characterization parts, for example, for the purpose of sorting cells, depending on the result of the characterization.

The feasibility of cell characterizations involving a cell manipulation and compression of cells under deformation has been known from, for example, (1) T. Baëtens, G. Perret, Y. Takayama, M. Kumemura, L. Jalabert, S. Meignan, C. Lagadec, F. Hiroyuki, D. Collard, and M. C. Tarhan, "*A practical single cell analysis method for mechanical characterization of cancer cells*," presented at the 2017 IEEE 30th International Conference on Micro Electro Mechanical Systems (MEMS, 2017, pp. 608-611), (2) G. Perret, Y. Takayama, M. Kumemura, S. Meignan, H. Fujita, C. Lagadec, D. Collard, and M. C. Tarhan, "Mechanical Characterization of Single Cells to Distinguish Different Breast Cancer Cells," presented at the 21st International conference on miniaturized systems for chemistry and life science, 2017, pp. 826-827, (3) Y. Takayama, G. Perret, M. Kumemura, C. Lagadec, S. Meignan, M. Ataka, H. Fujita, M. C. Tarhan, and D. Collard, "*Simultaneous electrical and mechanical characterization of single cells by an integrated device*," presented at the Micro Electro Mechanical Systems (MEMS), 2018 IEEE 31th International Conference on, 2018, pp. 297-300, and (4) Y. Takayama, G. Perret, M. Kumemura, M. Ataka, S. Meignan, S. Karsten, H. Fujita, D. Collard, C. Lagadec, and M. Tarhan, "*Developing a MEMS Device with Built-in Microfluidics for Biophysical Single Cell Characterization*," Micromachines, vol. 9, no. 6, pp. 275-14, Jun. 2018.

The invention claimed is:

1. A measuring device for measuring physical characteristics of cells, the measuring device comprising:
   a microfluidic chip provided with a flow channel for allowing cells to flow through from one end to another end of the flow channel, the flow channel including an inlet part, a characterization part and an outlet part;
   a manipulator situated in the characterization part between the inlet part and the outlet part of the flow channel and configured to manipulate a cell in a continuous flow through the characterization part by applying deformation force to the cell in the characterization part; and
   a sensor situated in the characterization part and configured to sense a physical characteristic of the cell in the characterization part of the flow channel,
   wherein the manipulator and the sensor are configured to define a width of the characterization part of the flow channel as a gap formed between the manipulator and the sensor, the width being smaller than a size of the cell, and
   wherein the manipulator is configured to apply the deformation force to the cell by compressing the cell against the sensor,
   wherein the manipulator comprises a guiding portion and a tip portion, the guiding portion being inclined toward the sensor to define a decreasing gap between the manipulator and the sensor, the tip portion extending parallel to the sensor to define a constant gap between the manipulator and the sensor,
   further comprising a further sensor situated in the inlet part which is upstream of the characterization part and configured to detect the size of a cell in the inlet part of the flow channel,
   wherein the manipulator is configured to control a position of the movable unit within the flow channel to adjust the width of the characterization part of the flow channel, depending on the size of the cell detected by the further sensor.

2. The measuring device according to claim 1, wherein the manipulator comprises a movable unit configured to move within the flow channel relative to the sensor so that the width of the characterization part of the flow channel is variable.

3. The measuring device according to claim 2, wherein the manipulator extends over a distance ranging from 10 μm to 1000 μm along the flow channel.

4. The measuring device according to claim 1, wherein the manipulator comprises a protrusion protruding within the flow channel, the protrusion protruding toward the sensor such that the width of the characterization part of the flow channel is formed as a gap formed between the protrusion and the sensor.

5. The measuring device according to claim 4, wherein the protrusion is configured such that the width of the characterization part of the flow channel gradually decreases along the flow channel.

6. The measuring device according to claim 4, wherein the manipulator extends over a distance ranging from 10 μm to 500 μm along the flow channel.

7. The measuring device according to claim 2, further comprising a further sensor situated in the inlet part which is upstream of the characterization part and configured to detect the size of a cell in the inlet part of the flow channel,
   wherein the manipulator is configured to control a position of the movable unit within the flow channel to adjust the width of the characterization part of the flow channel, depending on the size of the cell detected by the further sensor.

8. The measuring device according to claim 4, further comprising a further sensor configured to detect the size of a cell within the flow channel.

9. The measuring device according to claim 7, wherein the further sensor is configured to optically, magnetically or electrically detect the size of the cell.

10. The measuring device according to claim 1, wherein the sensor is further configured to sense mechanical and/or electrical characteristics of the cell in the characterization part of the flow channel.

11. The measuring device according to claim 1, wherein the sensor includes a plurality of electrodes.

12. The measuring device according to claim 1, further comprising at least one additional sensor and at least one additional manipulator, both of which are situated in an additional characterization part downstream of the characterization part of the flow channel.

13. The measuring device according to claim 12, wherein the at least one additional manipulator is configured to apply deformation force to the cell in the additional characterization part of the flow channel, the deformation force applied by the additional manipulator being different in magnitude from the deformation force applied by the manipulator.

14. A method for measuring physical characteristics of cells, comprising:
providing cells to a flow channel which is designed to allow the cells to continuously flow within the flow channel,
detecting a size of a cell flowing within the flow channel;
compressing the cell in a continuous flow in the follow channel by a portion of the flow channel whose width is defined by a gap between a manipulator and a sensor, the width being smaller than the size of the cell; and
sensing mechanical and/or electrical characteristics of the cell by the sensor, while compressing the cell between the manipulator and the sensor.

15. The method according to claim 14, wherein the compressing includes controlling deformation force applied by the manipulator to the cell, depending on the size of the cell detected prior to the compressing.

16. The measuring device according to claim 8, wherein the further sensor is configured to optically, magnetically or electrically detect the size of the cell.

* * * * *